United States Patent
Morrison et al.

(10) Patent No.: US 6,296,642 B1
(45) Date of Patent: Oct. 2, 2001

(54) REVERSE ANGLE THREAD FOR PREVENTING SPLAYING IN MEDICAL DEVICES

(75) Inventors: Matthew M. Morrison, Cordova; Craig Squires; B. Thomas Barker, both of Memphis, all of TN (US)

(73) Assignee: SDGI Holdings, Inc., Memphis, TN (US)

( * ) Notice: Subject to any disclaimer, the term of this patent is extended or adjusted under 35 U.S.C. 154(b) by 0 days.

(21) Appl. No.: 09/188,825

(22) Filed: Nov. 9, 1998

(51) Int. Cl.⁷ .................................................. A61B 17/56
(52) U.S. Cl. ............................................... 606/61; 606/73
(58) Field of Search .................................. 606/61, 62, 59, 606/63, 66, 73; 623/17; 285/332.3

(56) References Cited

U.S. PATENT DOCUMENTS

| | | | |
|---|---|---|---|
| 3,640,416 | * 2/1972 | Temple | 215/43 |
| 4,041,939 | 8/1977 | Hall | 128/69 |
| 4,653,486 | * 3/1987 | Coker | 606/65 |
| 4,707,001 | * 11/1987 | Johnson | 285/332.3 |
| 4,950,269 | 8/1990 | Gaines, Jr. | 606/61 |
| 5,005,562 | * 4/1991 | Cotrel | 606/61 |
| 5,034,011 | 7/1991 | Howland | 606/61 |
| 5,102,412 | 4/1992 | Rogozinski et al. | 606/61 |
| 5,147,363 | 9/1992 | Harle | 606/73 |
| 5,306,275 | 4/1994 | Bryan | 606/61 |
| 5,321,901 | * 6/1994 | Kelly | 36/134 |
| 5,468,241 | 11/1995 | Metz-Stavenhagen et al. | 606/61 |
| 5,474,555 | 12/1995 | Puno et al. | 606/61 |
| 5,490,750 | * 2/1996 | Gundy | 411/55 |
| 5,507,745 | 4/1996 | Logroscino et al. | 606/61 |
| 5,562,663 | 10/1996 | Wisnewski et al. | 606/61 |
| 5,569,251 | * 10/1996 | Baker et al. | 606/69 |
| 5,601,553 | * 2/1997 | Trebing et al. | 606/61 |
| 5,607,304 | * 3/1997 | Bailey et al. | 433/174 |
| 5,607,425 | 3/1997 | Rogozinski et al. | 606/61 |
| 5,607,428 | 3/1997 | Lin | 606/69 |
| 5,611,800 | 3/1997 | Davis et al. | 606/61 |
| 5,628,740 | 5/1997 | Mullane | 606/61 |
| 5,641,256 | * 6/1997 | Gundy | 411/55 |
| 5,662,653 | 9/1997 | Songer et al. | 606/61 |
| 5,672,176 | 9/1997 | Biedermann et al. | 606/61 |
| 5,683,390 | * 11/1997 | Metz-Stavenhagen et al. | 606/61 |
| 5,697,929 | * 12/1997 | Mellinger | 606/61 |
| 5,711,709 | * 1/1998 | McCoy | 464/406 |
| 5,723,013 | 3/1998 | Jeanson et al. | 623/17 |
| 5,725,527 | 3/1998 | Biedermann et al. | 606/61 |
| 5,728,098 | 3/1998 | Sherman et al. | 606/61 |
| 5,733,286 | 3/1998 | Errico et al. | 606/61 |
| 5,738,685 | 4/1998 | Halm et al. . | |
| 5,752,957 | * 5/1998 | Ralph et al. | 606/61 |
| 5,782,833 | 7/1998 | Haider | 606/61 |
| 5,797,911 | 8/1998 | Sherman et al. . | |

FOREIGN PATENT DOCUMENTS

| | | | |
|---|---|---|---|
| 298 06 563 U1 | 7/1998 | (DE) . | |
| 0885598 A2 | * 12/1998 | (EP) | 606/61 |

* cited by examiner

Primary Examiner—David O. Reip
Assistant Examiner—(Jackie) Tan-Uyen T. Ho
(74) Attorney, Agent, or Firm—Woodard, Emhardt, Naughton, Moriarty & McNett

(57) ABSTRACT

Apparatus is disclosed for use in closing a medical device and preventing splaying of wall portions or legs of the medical device while maintaining low profile and minimal bulk of the medical device. The disclosed device is a medical device including a receiver member and a closure member. The receiver member includes an internal reverse angle thread, and the closure member includes an outer reverse angle thread, matable with the inner reverse angle thread. When the closure member is threaded into the receiver member, forces tending to splaying the wall portions or legs of the receiver member cause an interference fit between thread surfaces of the closure member and the receiver member, preventing the splay from occurring.

33 Claims, 6 Drawing Sheets

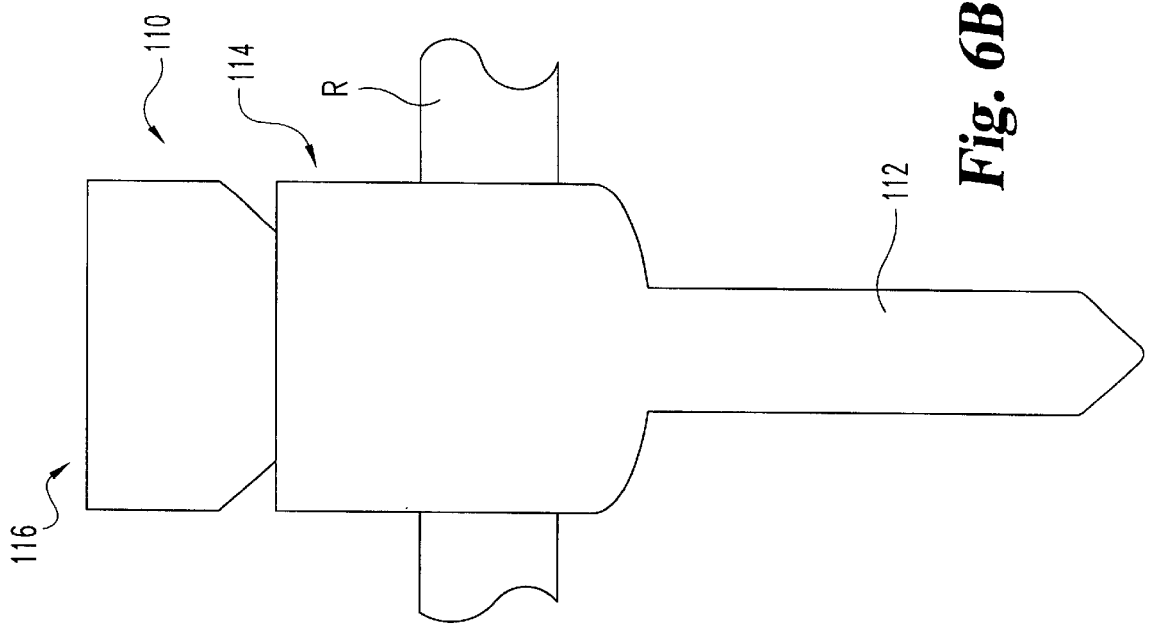
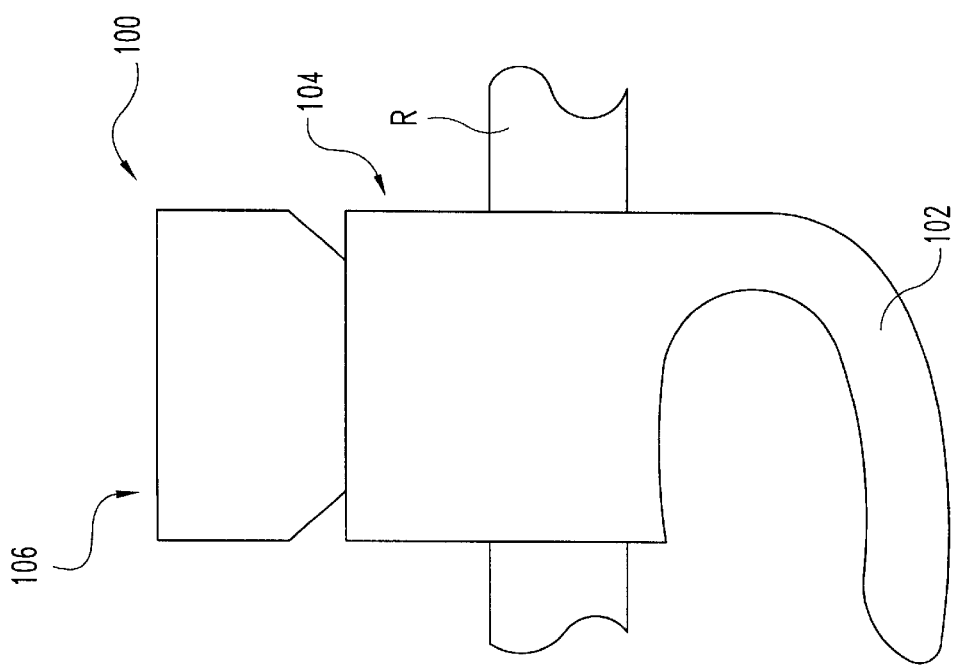

REVERSE ANGLE THREAD FOR PREVENTING SPLAYING IN MEDICAL DEVICES

FIELD OF THE INVENTION

The present invention relates to medical devices which utilize a threaded locking or closure element. More specifically, the invention relates to apparatus which is particularly useful in closing a medical device and preventing splaying of parts of the medical device.

BACKGROUND OF THE INVENTION

In the treatment of orthopedic injuries, diseases or deformities, it is well-known to place artificial implants in a patient's body to correct or improve his or her condition. Implant systems and devices are available to fix bones, muscles, tendons, and/or ligaments together or in a particular spatial relation so as to promote healing. For example, in the spinal field, one type of system for correcting and stabilizing the spine includes a bendable rod, which is preferably bent to correspond to the normal curvature of the spine in the particular region of interest. The rod is engaged to vertebrae along a length of the spinal column by way of a number of fixation elements. The variety of fixation elements configured to engage specific portions of the vertebrae includes hooks configured to engage the vertebral laminae and screws which can be threaded into parts of the vertebral bone. Rods or other similar elements can also be useful in correcting other orthopedic problems.

In several available rod-implantation systems, the rod is loaded into a channel in each fixation element. One example of such a system is the Cotrel-Dubosset/CD Spinal System sold by Sofamor Danek Group, Inc. The CD System includes hooks and bone screws with an "open-back"configuration, in which the fixation elements themselves include a body that defines a slot within which the spinal rod is received. The slot includes a threaded bore into which a threaded plug is engaged to clamp the rod within the body of the fixation element. Details of this technology can be found in U.S. Pat. No. 5,005,562 to Cotrel, the specification of which is hereby incorporated by reference. Other devices are also known which have a similar open-back configuration, such as those disclosed in U.S. Pat. Nos. 5,672,176, 5,725,527, 5,738,685, 5,782,833, and 5,728,098.

One difficulty that has been experienced with open-back configurations of medical devices is that the upright legs or wall sections of the body portion can experience splaying after implantation. For example, in the spinal field, after a rod is placed into the channel in the body portion of a open-back spinal fixation element, a closure or locking element is engaged in the body portion over the rod to clamp it within the channel so that there is no relative movement between the rod and the fixation element. Since no relative motion is possible, stresses placed on the rod after implantation are transmitted via the fixation element to the bone. In some cases, these stresses cause the legs or wall sections of the fixation element on either side of the slot to splay or move away from each other. Significant splaying of the fixation element generally results in its failure, since the closure or locking element can no longer be retained in the fixation element to clamp the rod. When that happens, the rod is free to move with respect to the fixation element, and may become disconnected with the fixation element altogether. In such a case, the therapeutic value of the implant is obviated, and further injury or complications may also result.

To prevent splaying, prior medical devices have included a nut, cap, clamp or similar apparatus to surround and hold the legs of the fixation element together. For example, in U.S. Pat. No. 5,672,176 to Biedermann et al., a rod is placed into a slot in the fixation element, the locking member is engaged with the fixation element to press down via an intermediary part on the rod, and an outer nut is threaded on the outside of the fixation element. Although effective in controlling splaying, these devices have tended to be relatively more expensive and less efficient to implant compared with devices without an outer nut or cap. The outer nut or cap also adds to the profile of the medical device, making the device more difficult to implant in the frequently limited area in which to perform surgery and/or place an implant. A larger implant can also result in a higher risk of residual pain to the patient or potential complications.

There is therefore a need remaining in the industry for medical devices, and particularly orthopedic devices, which minimize the profile and bulk of the components of the device and minimizes the cost and difficulty of using such devices, while still preventing splaying of the fixation elements.

SUMMARY OF THE INVENTION

According to one preferred embodiment of the present invention, a medical device is provided which includes a receiver member having a plurality of legs or wall sections that define a longitudinal bore and a transverse channel in the medical device, and a closure member having a substantially cylindrical engagement portion with a longitudinal axis. The closure member also includes a reverse angle thread, which engages the legs or wall sections of the medical device. The present invention can be a part of a variety of medical devices or tools in which a plurality of legs or wall sections have the potential to splay. In a particularly preferred embodiment, the invention is used with a bone screw, laminar hook, compression plate, external fixator or other bone fixation device in which two or more legs or wall sections define a rod-receiving channel and a bore communicating with the channel and which accommodates the closure member. The inner surfaces of the legs or wall sections, in a particular embodiment, also include reverse angle threads which are matable with the reverse angle thread on the closure member.

The reverse angle thread of the present invention has two surfaces, a forward-facing surface or clearance flank, and a rearward-facing surface or load flank. The rearward surface of the reverse angle thread is configured so that the angle between a plane normal to the longitudinal axis and the rearward surface, or pressure angle, is negative. That is, the crest of the thread points backwards, toward the proximal end of the closure member and receiver member. In one embodiment, the pressure angle is between −1 and −40 degrees. In a currently more-preferred embodiment, the pressure angle is −5 degrees. In another embodiment, the forward facing surface of the reverse thread forms a flank angle, measured from a plane normal to the longitudinal axis forward facing surface, of +45 degrees.

The present invention provides an apparatus in which a medical device is closed or locked and splaying of the medical device is prevented. The invention provides the further advantages of reducing the size and profile of the medical device. Not only does elimination of an outer nut or cap reduce the size, but the reverse angle thread allows the size of the receiver member itself to be significantly reduced without a greater risk of splaying. An additional benefit is the reduction in cost and the difficulty of implantation of such devices by eliminating unnecessary parts. Other benefits and certain objects of the invention will be appreciated by one of ordinary skill in the art and will become apparent upon consideration of the following written description and accompanying figures illustrating one embodiment of the present invention.

DESCRIPTION OF THE DRAWINGS

FIG. 6A is a side elevation of a laminar hook medical device with which an embodiment of the present invention is useful.

FIG. 6B is a side elevation of one type of bone screw medical device with which an embodiment of the present invention is useful.

DESCRIPTION OF THE PREFERRED EMBODIMENT

Figure 1:
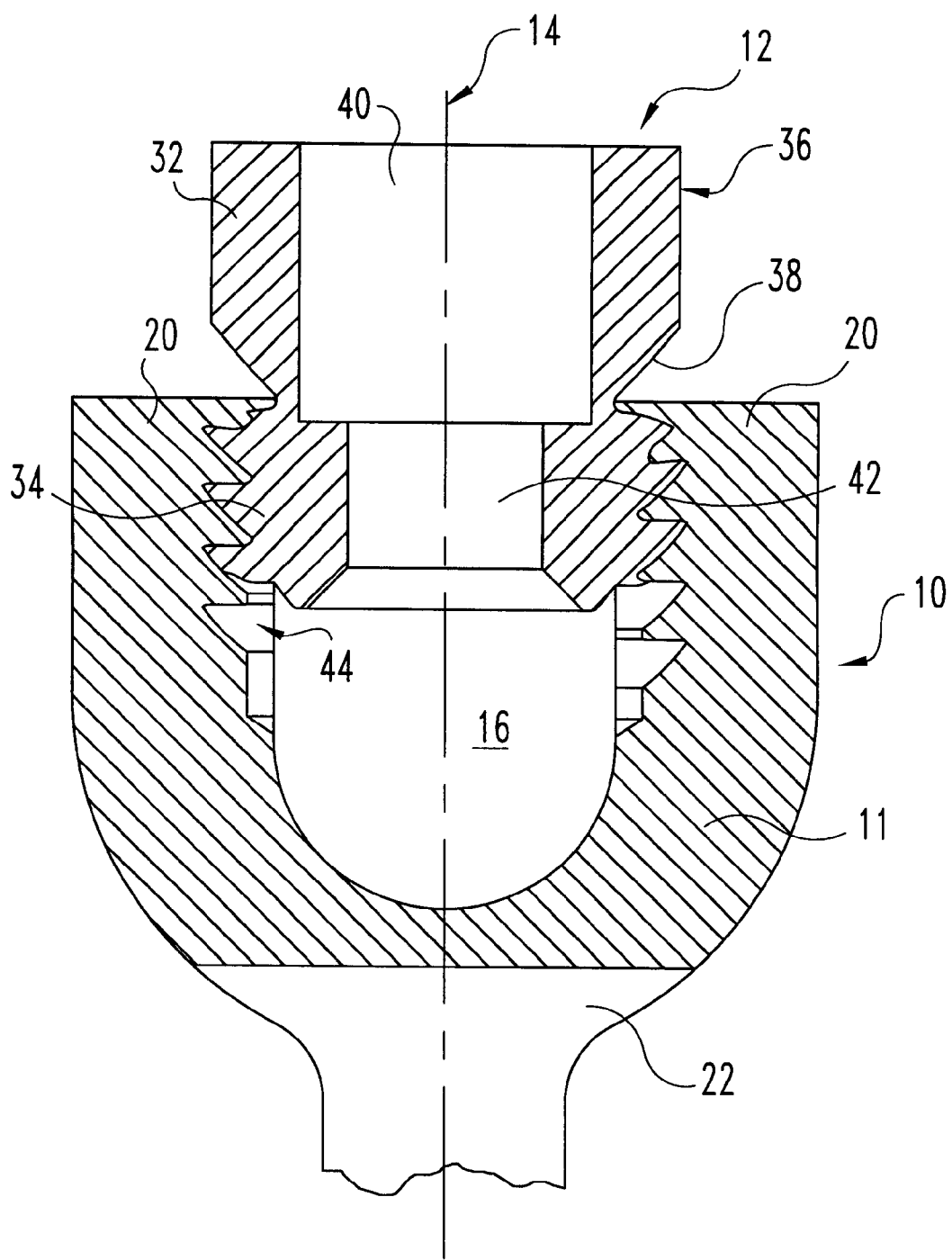
FIG. 1 is a fragmentary, part-sectional view of a preferred embodiment of the apparatus of the present invention.
Figure 2:
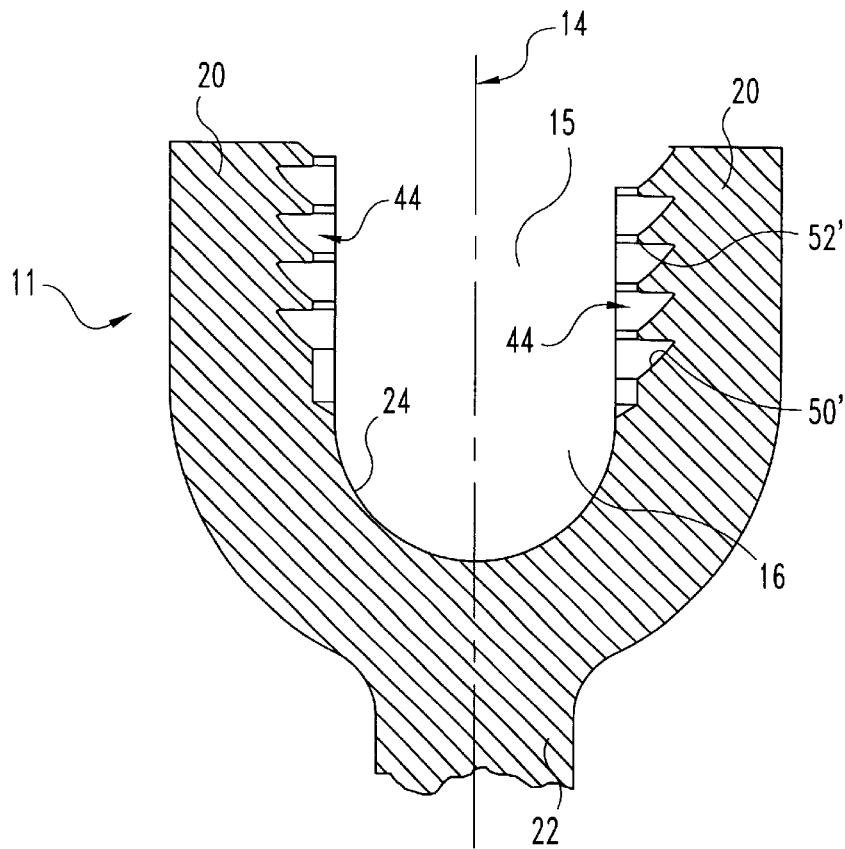
FIG. 2 is a sectional view of part of the receiver member of the embodiment of the apparatus of the present invention illustrated in FIG. 1.
Figure 3:
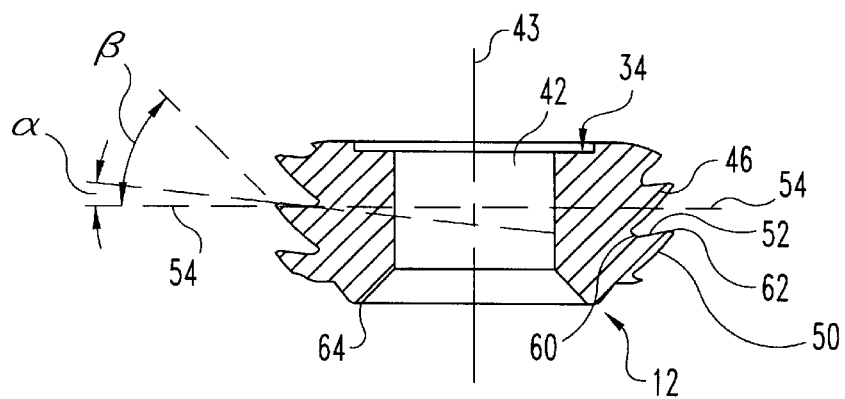
FIG. 3 is a sectional view of one embodiment of the closure member of the embodiment of the apparatus of the present invention illustrated in FIG. 1.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates.

Referring generally to FIGS. 1–5, there is shown a medical device 10 according to the present invention. As illustrated, medical device 10 includes a receiver member 11 and a closure member 12 adapted to be threadedly engaged to receiver member 11. Medical device 10, in the illustrated embodiment, is a bone fixation device used to connect an elongated member (indicated as R in FIGS. 4–6C) to a bone. In that embodiment, receiver member 11 includes a longitudinal or thread axis 14, a longitudinal bore 15 centered on axis 14, and a transverse channel 16 for receiving an elongated member, which is generally perpendicular to axis 14 and bore 15. Channel 16 is bounded on both sides by legs 20 of receiver member 11. Receiver member 11 further includes a fixation portion 22. Fixation portion 22, in a particular embodiment, is a threaded portion for threading into a bone, and in another embodiment (not shown) is a hook portion for connection to a bone.

Closure member 12, in a particular embodiment, includes a break-off section 32 and a screw section 34. Break-off section 32 has a generally cylindrical upper or proximal portion 36 and a thinned neck portion 38. Break-off section 32 and screw section 34 have holes 40 and 42, respectively, for engaging tools. In one specific embodiment, holes 40 and 42 have a hexagonal and star shape, respectively, although other known tool head shapes may be used. In this embodiment, closure member 12 is threadedly engaged with receiver member 11 to a point at which further threaded progression is impeded, as for example when the screw section 34 contacts an object within channel 16, such as rod R seated against wall 24. As further torque is applied to break-off screw closure member 12, as with an hexagonal driving tool inserted into hole 40, eventually the stress on the neck portion 38 is great enough to cause the upper section 36 to break off from screw section 34 at neck portion 38. In this way, screw section 34 is firmly seated in bore 15 of receiver member 11 against rod R in channel 16, and the excess material of the break-off screw, which assisted in the original threading, is removed.

Figure 4:
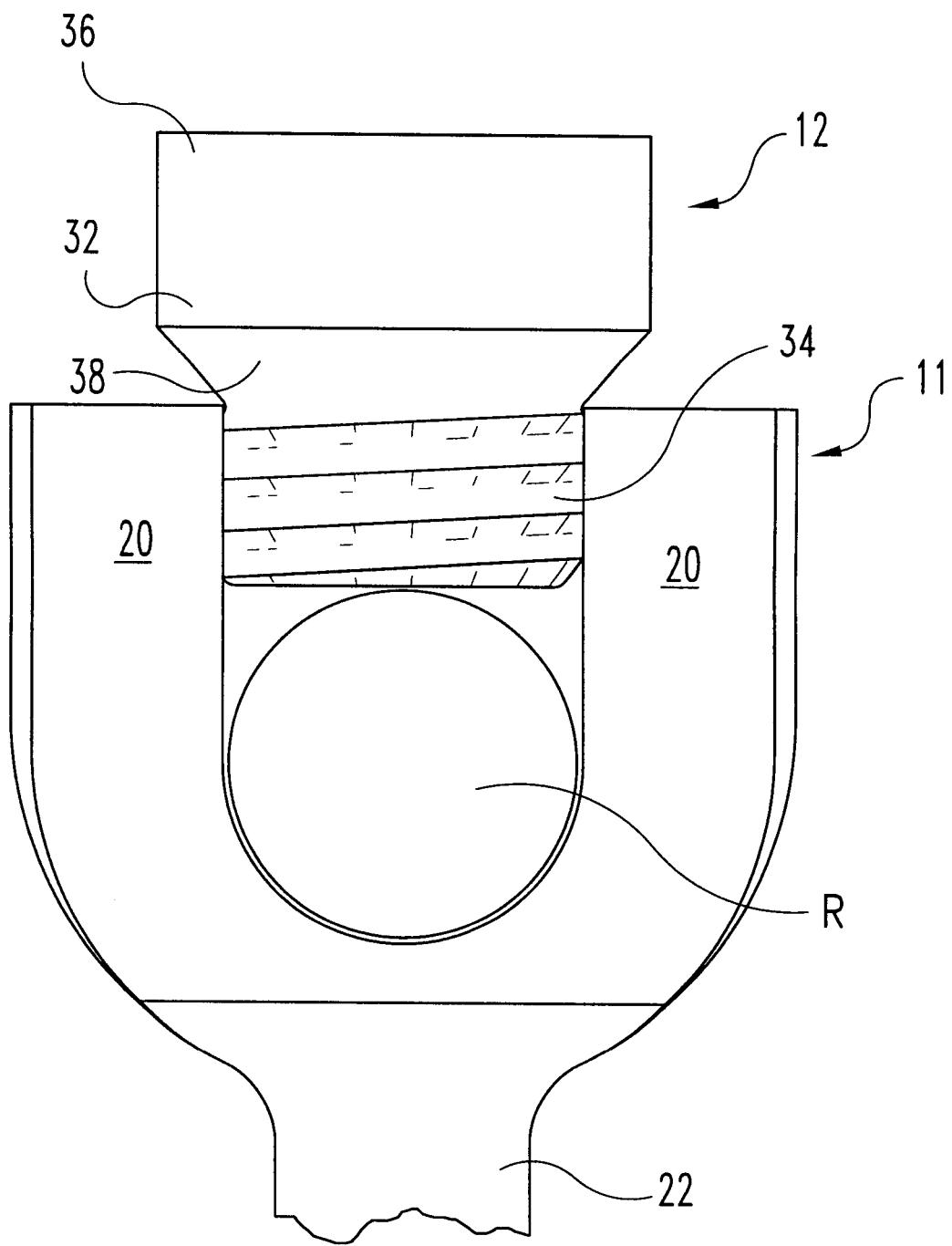
FIG. 4 is a front elevation of the embodiment of the present invention illustrated in FIG. 1, including an elongated member.
Figure 5:
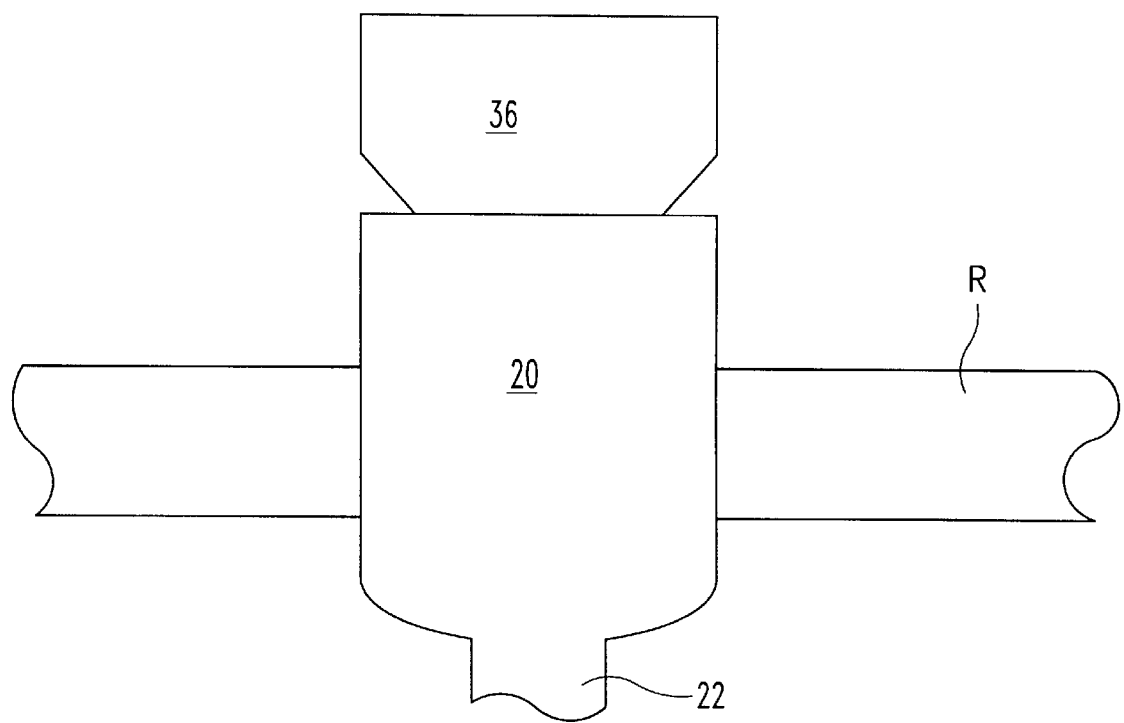
FIG. 5 is a side elevation of the embodiment of the present invention illustrated in FIG. 4.

In another particular embodiment of closure member 12, illustrated in FIG. 4, closure member 12 includes only screw section 34, which may be characterized as a set screw. Screw portion 34, and break-off section 32 if included in closure member 12 (as in FIGS. 1, 4 and 5), has a longitudinal axis 43. When closure member 12 and receiver member 11 are engaged, as illustrated in FIG. 1, longitudinal axis 43 of closure member 12 and longitudinal axis 14 of receiver member 11 are collinear.

Receiver member 11 includes an inner thread 44 inside legs 20, and screw section 34 of closure member 12 includes an outer thread 46. Threads 44 and 46 have substantially the same characteristics,'so that closure member 12 is threadably engageable with receiver member 11 by engaging threads 46 with thread 44. Threads 44 and 46 will be described by reference to thread 46, illustrated in FIG. 4. Threads 44 and 46 are reverse angle threads. As used herein, "reverse angle thread" refers to a thread wherein the rearward-facing thread surface or load flank is sloped so that, for a given cross-section of the thread through the longitudinal axis of the screw, a point on the rearward-facing thread surface at the root of the thread is closer to the distal or forward end of the screw than a point on the rearward-facing thread surface at the crest of the thread.

As shown in FIG. 4, closure member 12 has a reverse angle thread 46 including forward-facing thread surface 50 and rearward-facing thread surface 52. Thread 44 (see FIG. 2) has a corresponding forward thread surface 50' and a rearward thread surface 52'. Point 60, depicted in FIG. 4 at the root of rearward thread surface 52, is closer than point 62 (at the crest of rearward surface 52) to the forward end 64 of screw section 34. To define the angles of the thread surfaces, plane 54 normal to longitudinal axis 43 is also shown. As used herein, an angle measured clockwise from a normal plane (such as plane 54) to the rearward thread surface is a negative angle, and an angle measured clockwise from a normal plane (such as plane 54) to the forward thread surface is a positive angle. Thus, pressure angle a of thread 46 (illustrated in FIG. 4) is negative, since the measurement is clockwise from the thread root at plane 54 to rearward thread surface 52, as indicated by the arrow. Flank angle P in FIG. 4, representing the clockwise angle from plane 54 to forward thread surface 50, is positive.

Accordingly, a reverse angle thread includes a rearward surface such that α is a negative angle.

In one particular embodiment of the present invention, illustrated in FIG. 4, pressure angle α is −5 degrees, and flank angle β is 45 degrees. However, it is understood that one of ordinary skill in the art will recognize that other negative values of pressure angle α, including values between about −1 degree and at least −40 degrees, and other values of flank angle β are within the scope of the present invention. As noted above, reverse angle thread 44 of receiver member 11 is configured substantially similarly to reverse angle thread 46 of closure member 12 so that threads 44 and 46 can be engaged. Accordingly, rearward thread surface 52' of thread 44 forms a negative pressure angle, i.e., one measured clockwise from a plane normal to axis 14 to rearward thread surface 52', of substantially the same magnitude as pressure angle a illustrated in FIG. 4. Forward thread surface 50' of thread 44 (FIG. 2) forms a positive flank angle of substantially the same magnitude as flank angle β illustrated in FIG. 4.

In use, closure member 12 is threaded into receiver member 11 such that reverse angle thread 46 of closure member 12 is engaged with reverse angle thread 44 of receiver member 11. When closure member 12 and receiver member 11 are threadedly engaged, rearward thread surface 52 of closure member 12 will abut rearward thread surface 52' of receiver member 11, and forward thread surface 50 of closure member 12 will abut forward thread surface 50' of receiver member 11. Any force tending to splay legs 20, such as a force outward from and perpendicular to axis 14 of FIG. 2, will tend to move rearward thread surface 52' of receiver member 11 against and into an interference fit with rearward thread surface 52 of closure member 12. The abutment of rearward thread surfaces 52 and 52' prevent splaying of legs 20 outward from longitudinal axis 14 of receiver member 11.

Figure 6C:
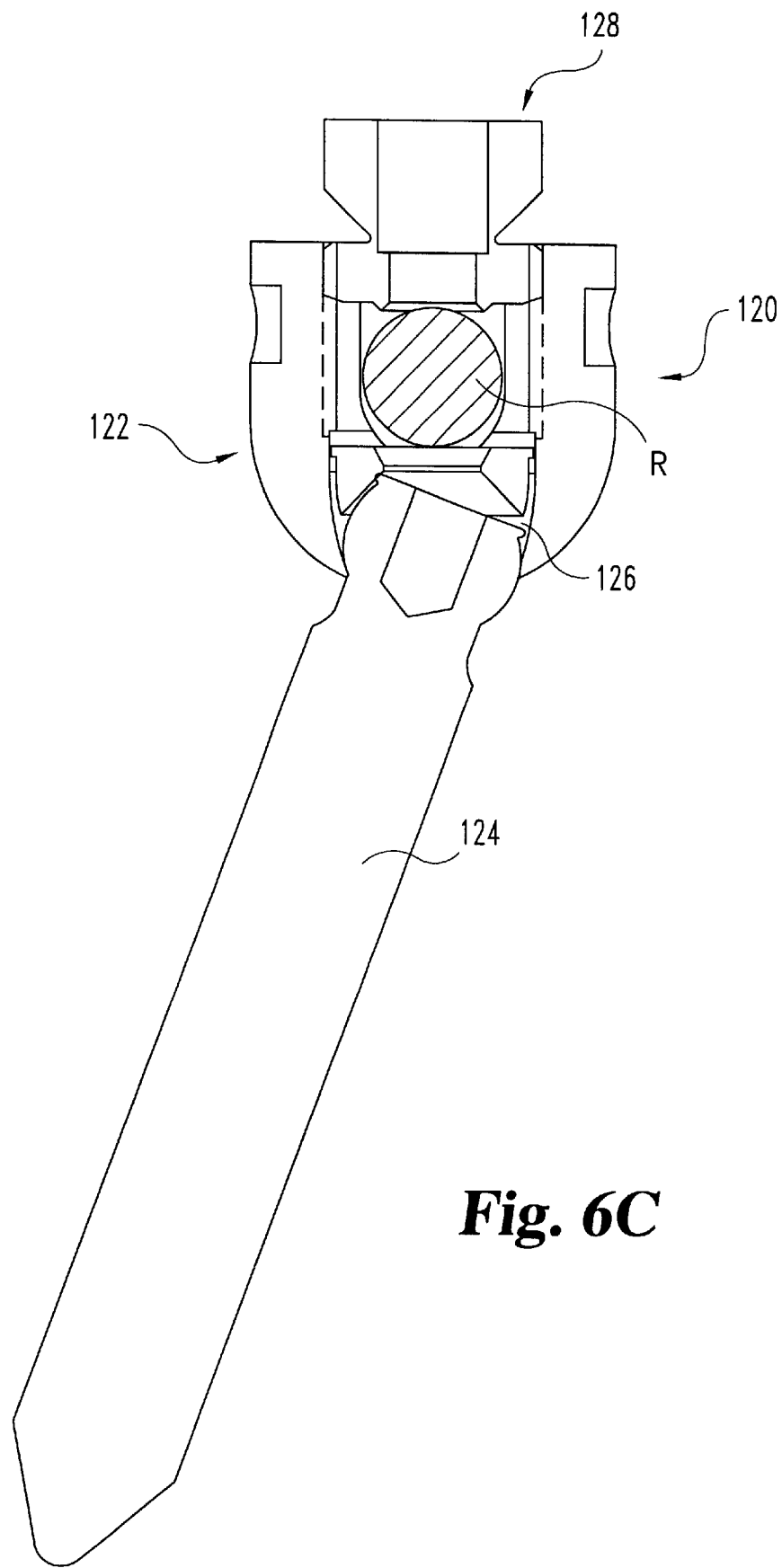
FIG. 6C is a side elevation of one type of multi-axial bone screw medical device with which incorporates an embodiment of the present invention is useful.

It will be appreciated that any medical device which includes a holder or receiver member that tends to splay can incorporate the present invention. As indicated above, in a preferred embodiment of the present invention medical device 10 is a bone fixation device for connecting an elongated member and a bone, and particularly an "open-back" bone fixation device. Examples of such devices are illustrated in FIGS. 6A–6C. FIG. 6A illustrates an open-back laminar hook 100 having an integral U-shaped bone fixation portion 102, and FIG. 6B illustrates an open-back bone screw 110 having an integral threaded bone fixation portion 112. Hook 100 and screw 110 include receiver members 104 and 114, respectively, which are substantially similar to receiver member 11 depicted in FIG. 1, and are thus able to receive rod R in a seated engagement. Hook 100 and screw 110 also include closure members 106 and 116, respectively, which are substantially similar to closure member 12 of FIG. 1, and thus operate in the same manner as described above with respect to the embodiment of the invention illustrated in FIGS. 1–5.

In the realm of bone fixation devices, the present invention may also be used in connection with a multi-axial bone screw or bone hook system in which the fixation element is rotatable within a body element. One example of such a system is found in U.S. Pat. No. 5,797,911 to Sherman, et al., owned by the Assignee of the present invention, the specification of which is hereby incorporated by reference herein and an embodiment of which is illustrated in FIG. 6C. Multi-axial device 120 includes a receiver member 122 similar to receiver member 11 of FIG. 1, the principal differences being that bone fixation portion 124 (illustrated as a bone screw in FIG. 6C) of multi-axial device 120 is not integral with receiver member 122, and is free to rotate within bore 126 which extends from top to bottom through receiver member 122. Multi-axial device 120 also includes a closure member 128 which is substantially similar to closure member 12 of FIG. 1, and thus operates in the same manner as described above with respect to the embodiment of the invention illustrated in FIGS. 1–5.

It is preferred that both closure member 12 and receiver member 11 be manufactured from bio-compatible materials, and preferably metals such as titanium or stainless steel. It is also preferred that the reverse angle thread be formed integrally on the outside of closure member 12 and on the inside of receiver member 11 prior to the use of the medical device. However, forming an integral reverse angle thread 44 on the inside of receiver member 11 prior to use is not strictly necessary, so long as closure member 12 can be twisted into receiver member 11 so that reverse angle thread 46 of closure member 12 gouges the insides of legs 20 to form a threaded engagement between closure member 12 and receiver member 11.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A medical device, comprising:
   a receiver member including a plurality of wall sections defining a longitudinal bore in said medical device, said receiver member also including a transverse channel substantially perpendicular to said bore; and
   a closure member including a substantially cylindrical engagement portion having a longitudinal axis, and a reverse angle thread formed on said engagement portion so that said engagement portion is adapted to be threadedly engaged within said bore to said wall sections.

2. The medical device of claim 1, wherein said wall sections include an inner reverse angle thread corresponding to said reverse angle thread of said engagement portion of said closure member, whereby said reverse angle thread of said wall sections and said reverse angle thread of said engagement portion are engaged when said engagement portion is threadedly engaged within said bore to said wall sections.

3. The medical device of claim 1, wherein said receiver member is a part of a bone fixation device.

4. The medical device of claim 3, wherein said bone fixation device is a bone screw.

5. The medical device of claim 4, wherein said bone fixation device is a multi-axial bone screw.

6. The medical device of claim 3, wherein said bone fixation device is a spinal hook.

7. The medical device of claim 3, wherein said reverse angle thread includes a rearward thread surface, wherein an angle measured from a plane normal with said longitudinal axis to said rearward thread surface is between about −1 degrees and −40 degrees.

8. The medical device of claim 7, wherein said angle is about −5 degrees.

9. The medical device of claim 1, wherein said closure member is a set screw.

10. The medical device of claim 1, wherein said closure member is a break-off screw.

11. An apparatus for connecting an elongated member and a bone, comprising:
    a receiver member having an inner-threaded longitudinal bore, a channel communicating with and substantially perpendicular to said longitudinal bore for accommodating the elongated member and a fixation portion for fixing said receiver member to the bone; and
    a closure member having a longitudinal axis and an outer threaded portion for threaded engagement with said threaded portion of said receiver member, wherein said threaded portion of said receiver member and said threaded portion of said closure member include a reverse angle thread.

12. The apparatus of claim 11, wherein said reverse angle thread of said closure member includes a rearward thread surface such that an angle measured from a plane normal with said longitudinal axis to said rearward thread surface of said closure member is between about −1 degrees and −40 degrees, and said reverse angle thread of said receiver member includes a rearward thread surface such that an angle measured from a plane normal with an axis of said longitudinal bore to said rearward thread surface of said receiver member is between about −1 degrees and −40 degrees.

13. The apparatus of claim 12 wherein said closure member is a set screw.

14. The apparatus of claim 12 wherein said closure member is a break-off head screw.

15. The apparatus of claim 11 wherein said fixation portion is integral with said receiver member.

16. The apparatus of claim 15 wherein said fixation portion includes a threaded portion.

17. The apparatus of claim 15 wherein said fixation portion includes a hook portion.

18. The apparatus of claim 11 wherein said bore of said receiver member extends through said receiver member, and said fixation portion is a bone fixation device which is accommodated within at least a portion of said bore and is adaptable to be fixed to the bone at any of a plurality of angles to said bore.

19. The apparatus of claim 18 wherein said bone fixation device is a bone screw.

20. The apparatus of claim 18 wherein said bone fixation device is a hook.

21. A medical device, comprising:
a receiver member including a plurality of wall sections separated by a slot, said wall sections at least partially defining a longitudinal bore in said medical device; and
a closure member including a substantially cylindrical engagement portion having a longitudinal axis, and a reverse angle thread formed on said engagement portion so that said engagement portion is adapted to be threadedly engaged within said bore to said wall sections.

22. The medical device of claim 21, wherein said wall sections include an inner reverse angle thread corresponding to said reverse angle thread of said engagement portion of said closure member, whereby said reverse angle thread of said wall sections and said reverse angle thread of said engagement portion are engaged when said engagement portion is threadedly engaged within said bore to said wall sections.

23. The medical device of claim 21, wherein said receiver member includes a transverse channel substantially perpendicular to said longitudinal bore of said receiver member.

24. The medical device of claim 21, wherein said receiver member is a part of a bone fixation device.

25. The medical device of claim 24, wherein said bone fixation device is a bone screw.

26. The medical device of claim 25, wherein said bone fixation device is a multi-axial bone screw.

27. The medical device of claim 24, wherein said bone fixation device is a spinal hook.

28. The medical device of claim 24, wherein said reverse angle thread includes a rearward thread surface, wherein an angle measured from a plane normal with said longitudinal axis to said rearward thread surface is between about −1 degrees and −40 degrees.

29. The medical device of claim 28, wherein said angle is about −5 degrees.

30. The medical device of claim 21, wherein said closure member is a set screw.

31. The medical device of claim 21, wherein said closure member is a break-off screw.

32. The medical device of claim 21, wherein a plurality of slots separate said wall sections.

33. The medical device of claim 32, wherein said plurality of slots form at least one channel transverse to said longitudinal bore.

* * * * *